United States Patent
Morávek

(10) Patent No.: US 6,616,645 B1
(45) Date of Patent: Sep. 9, 2003

(54) ABSORBENT DIAPER PANTS FOR CHILDREN WITH THERAPEUTIC ORTHOPAEDIC PAD

(76) Inventor: Zdeněk Morávek, Sv. Cecha 678, 551 01 Jaromer (CZ)

(*) Notice: Subject to any disclaimer, the term of this patent is extended or adjusted under 35 U.S.C. 154(b) by 0 days.

(21) Appl. No.: 09/856,421
(22) PCT Filed: Feb. 1, 1999
(86) PCT No.: PCT/CZ99/00003
§ 371 (c)(1), (2), (4) Date: Jun. 28, 2001
(87) PCT Pub. No.: WO00/30573
PCT Pub. Date: Jun. 2, 2000

(30) Foreign Application Priority Data

Nov. 20, 1998 (CZ) .............................. 3787-98

(51) Int. Cl.$^7$ .............................. A61F 13/15
(52) U.S. Cl. .............. 604/385.06; 602/24; 604/385.14; 604/385.01; 604/395; 604/398; 604/385.24; 604/385.3; 604/385.28; 604/385.23
(58) Field of Search ............ 604/385.14, 385.01, 604/395, 398, 385.06, 385.24, 385.3, 385.28, 385.23; 602/24

(56) References Cited

U.S. PATENT DOCUMENTS

| 4,393,865 A | 7/1983 | Lambert |
|---|---|---|
| 4,961,737 A | 10/1990 | Orlando |
| 5,618,264 A | 4/1997 | Vasquez |

FOREIGN PATENT DOCUMENTS

EP 0277261 8/1988

*Primary Examiner*—Rodney M. Lindsey
*Assistant Examiner*—Angela J Grayson
(74) *Attorney, Agent, or Firm*—Ostrolenk, Faber, Gerb & Soffen, LLP

(57) ABSTRACT

Absorbent diaper pants having a front part (2), a back part (3) with an elastic member (20) in the waist hole (12) region, and a crotch part (4) with elastic hems (19) in the diaper pants (1) leg holes (13), wherein the front part (2) and the back part (3) are provided with fastening means (21), and on the diaper pants (1) inner surface side a changeable absorbent pad (14) is arranged, and the diaper pants (1) are further provided with a therapeutic orthopaedic pad (29); characterized in that the orthopaedic pad (29) is located in a rectangular housing (27) arranged on the diaper pants (1) facing side, while this housing (27) is by its front and back transverse ends, in a takeable apart manner, secured to the end edges (9, 10) of the front part (2) and of the back part (3), and the absorbent pad (14) is inserted inside retaining means.

12 Claims, 3 Drawing Sheets

ABSORBENT DIAPER PANTS FOR CHILDREN WITH THERAPEUTIC ORTHOPAEDIC PAD

FIELD OF THE INVENTION

The invention relates to a panty-like type absorbent diaper destined for repeated use and provided for that purpose with a changeable absorbent pad. The diaper pants comprise a front part, a back part and a crotch part with an absorbent pad, while the front and back parts are extended to side portions with fastening means.

BACKGROUND OF THE INVENTION

The multipurpose diaper panties with an absorbent body have been known, being repeatedly used either as a commonly worn underpants or serving as a diaper. The body liquids are absorbed in the same manner as in a common diaper case, but the panty-like pants serve further to its user in an intact condition until the time and an opportunity come to replace the soiled panty-like diaper with a clean diaper. As the user is to have a feeling of wearing underclothes, it is important that the panty-like diaper is of a panties shape, e.i., the article with a waist and leg openings, not a pants form with fastening tabs connecting during application the diaper front and back parts. As well as the outer casing layer materials for the panty-like diaper are selected such that above all the adult users are spared of psychologically negative feelings during wearing a diaper with a plastic outer casing layer.

In case the panty-like diaper is worn by children (babies) other problems occur upon the basis of a fact that a fair number of children suffer from hip joints deformations, e.g., dysplasia, and on that reason they have to wear for a longer period health aids for their treatment. For that purpose greater number of diapers have been commonly used instead of a usual single diaper, but that brings about difficulties with diapers displacement and their deflection from a desired position between children's thighs during wear, or special therapeutic aids are applied over common diapers. So there is known, e.g., a side splint for correcting hip dysplasia in a harness form with rains, which system is fastened against the child's body. In order to obtain a necessary lean out of the babies' thighs a semi-rigid longitudinal portion is used, continuous in the back part and divided in the front part into two side portions embracing the child's thighs and secured to the harness waist region. In another embodiment the semi-rigid portion is formed as having an increased front and back parts with reins and a central crotch part with side portions embracing the child's thighs and fixable in a position turned around the thighs with small strips. Wearing the therapeutic aids of this kind presents a very uncomfortable task for a child. As well as the replacing of soiled diapers is complicated by a necessary release and refastening of the therapeutic aid.

U.S. Pat. No. 4,393,865 discloses a diaper for small babies destined to prevent or treat abnormalities of one or both hips, for example, dysplasia or joints subluxation. The diaper contains semi-rigid padding means which are parts of the diaper material and intended for the baby's thighs orientation into a desired position with an inclination taking into consideration pelvis and side deflection. To fix the above mentioned semi-rigid orientation means on the baby's body the diaper includes flexible closures. The orientation semi-rigid means can be destined, e.g., for treating the inflammations of the small of the back and sacral nerves and they are then positioned at the back body part, or they can be destined for inflammatory illnesses of a pubic bone and then oriented in this region with the front side located between the baby's thighs. The diaper can be supplemented or combined with common absorbent means such as triangle diapers, diaper panties or disposable diapers. For example, with the orientation means for treating the small of the back and sacral nerves inflammations the diaper can contain absorbent means incorporated into an absorbent padding arranged as a diaper part in the vicinity of the diaper centerline, or it can contain a separate absorbent body with retaining means by which it can be attached to the diaper substrate, e.g., by welding or to be glued to it. In this case the absorbent body is located above the transverse orientation member. But said diaper is apt to slippage or turning out from the position between the baby's thigh when used. The diaper is made of polyurethan which is not especially useful as an absorbent means for absorbing discharged body fluids and makes cleaning and drying of the diaper rather difficult. The diaper fastening means, horizontal ones, do not prevent the diaper to drop off the user's waist, so the semi-rigid or padding means are not correctly placed.

From U.S. Pat. No. 4,961,737 a therapeutic diaper is known containing the main longitudinal panel from an elastic material having an inner and outer layers between which an internal pocket is found. On the opposite longwise edges of the longitudinal panel, at the panel short side, there are flexible side arms with fastening means for corresponding fasteners on the longitudinal panel outer surface at its second shorter side, for releasable fastening of the diaper on the user's body. In the longitudinal panel inner pocket a combined padding and an absorbent body is located with dimensions providing for fastening and holding the diaper in a flexible, or a closely similar position, and for body liquids absorption. At the longitudinal panel lengthwise edges elastic strips can be arranged to seal the panel around the user's legs and the slip of the diaper. The diaper when used is located in a manner that the longitudinal panel runs back from the user's back waist region down to the crotch and again upwards to the waist region on the opposite part of the body, with inner layer against the user's skin, while the flexible side arms extend from the back waist region forward and diagonally down and here their fastening means are secured to the fasteners on the outer surface of the longitudinal panel. The absorbent pad is a combined body made of a common absorbent and padding material with good absorbency, easily laundered, washable and driable, and repeatedly used. Although such a diaper serves both to therapeutic and common purposes, maintaining it in an applicable clean and dry condition, however, is time consuming and it is not applicable separately to individual purposes.

SUMMARY OF THE INVENTION

The above mentioned drawbacks are solved with the absorbent diaper pants according to the invention.

The absorbent diaper panties have a front part, a back part with an elastic member in the waist hole region, and a crotch part with elastic hems in the diaper pants leg holes, wherein the front part and the back part are provided with fastening means, and on the diaper pants inner surface side a changeable absorbent pad is arranged. The diaper pants are further provided with a therapeutic orthopaedic pad characterised in that the orthopaedic pad is located in a rectangular housing arranged on the diaper pants facing side, while this housing is by its front and back transverse end ends, in a takeable apart manner, secured to the end edges of the front part and of the back part and the absorbent pad is inserted inside retaining means.

According to a favourable embodiment of the invention the orthopaedic pad is made of a firm elastic material and arranged changeably in the rectangular housing.

According to another favourable embodiment of the invention the rectangular housing has a longitudinal dimension corresponding to the diaper panties length and a transverse dimension corresponding to its front part width, being closed at its front transverse end edge, adjacent to the front part end edge, while the opposite back transverse end edge, adjacent to the back part end edge, is open, and the rectangular housing is on both transverse end edges provided with fastening means for its securing to the diaper pants.

According to a yet another favourable embodiment of the invention the fastening means of the rectangular housing are formed by buttons, secured on the diaper pants front and back parts end edges, while the holes for the buttons are made in the corners of the front and back end transverse edges of the rectangular housing.

According to other favourable embodiment of the invention the absorbent diaper retaining means are formed by two bands extending over the whole width of the panties front and back parts and being anchored in the side and end edges of the front and back parts, while the inner transverse edges of the bands are free with the bands thus forming pockets for inserting the absorbent pad.

The absorbent diaper panties according to the invention maintain properties of known diaper pants with a changeable absorbent pad. The diaper pants holding system is very simple and provides for sufficient strength and elasticity of the panties and exclude their spontaneous opening. Even the not absorbed body fluids discharge is prevented, as well as soiling the user's clothing. The diaper panties can serve as pants, diaper pants or diaper pants with an orthopaedic pad for prevention and abnormalities treatment. The orthopaedic pad is of such a size and location that it sits safely on a desired place when used.

BRIEF DESCRIPTION OF THE DRAWINGS

Absorbent diaper pants exemplary embodiments are shown in the accompanying drawings, wherein.

DETAILED DESCRIPTION OF THE INVENTION

Figure 1:
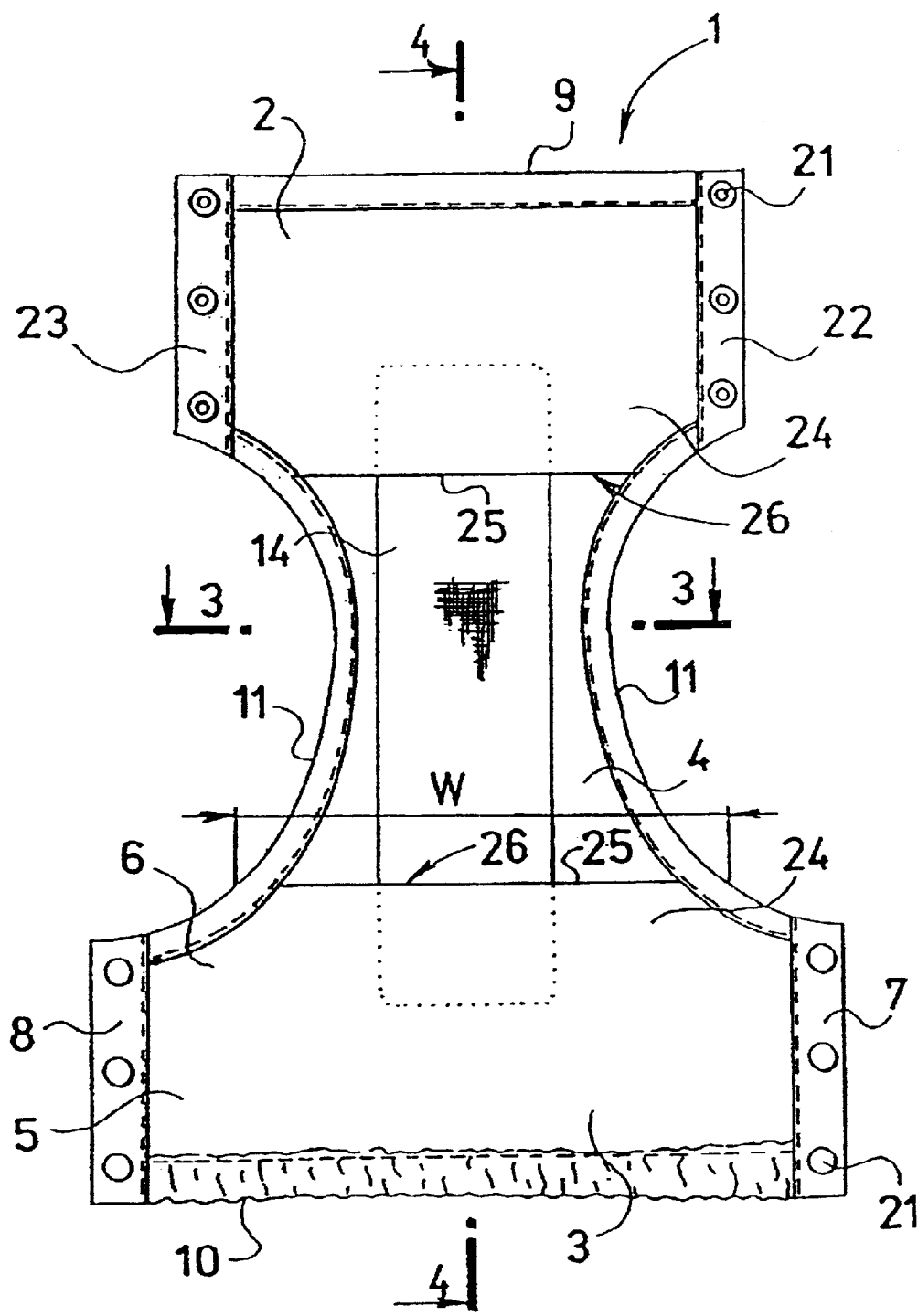
FIG. 1—shows a diaper pants from above, prior to use, with not yet formed waist nor leg openings.

The absorbent diaper pants, shown on FIG. 1, are in a prior to use condition, with not yet formed waist nor leg openings.

Figure 2:
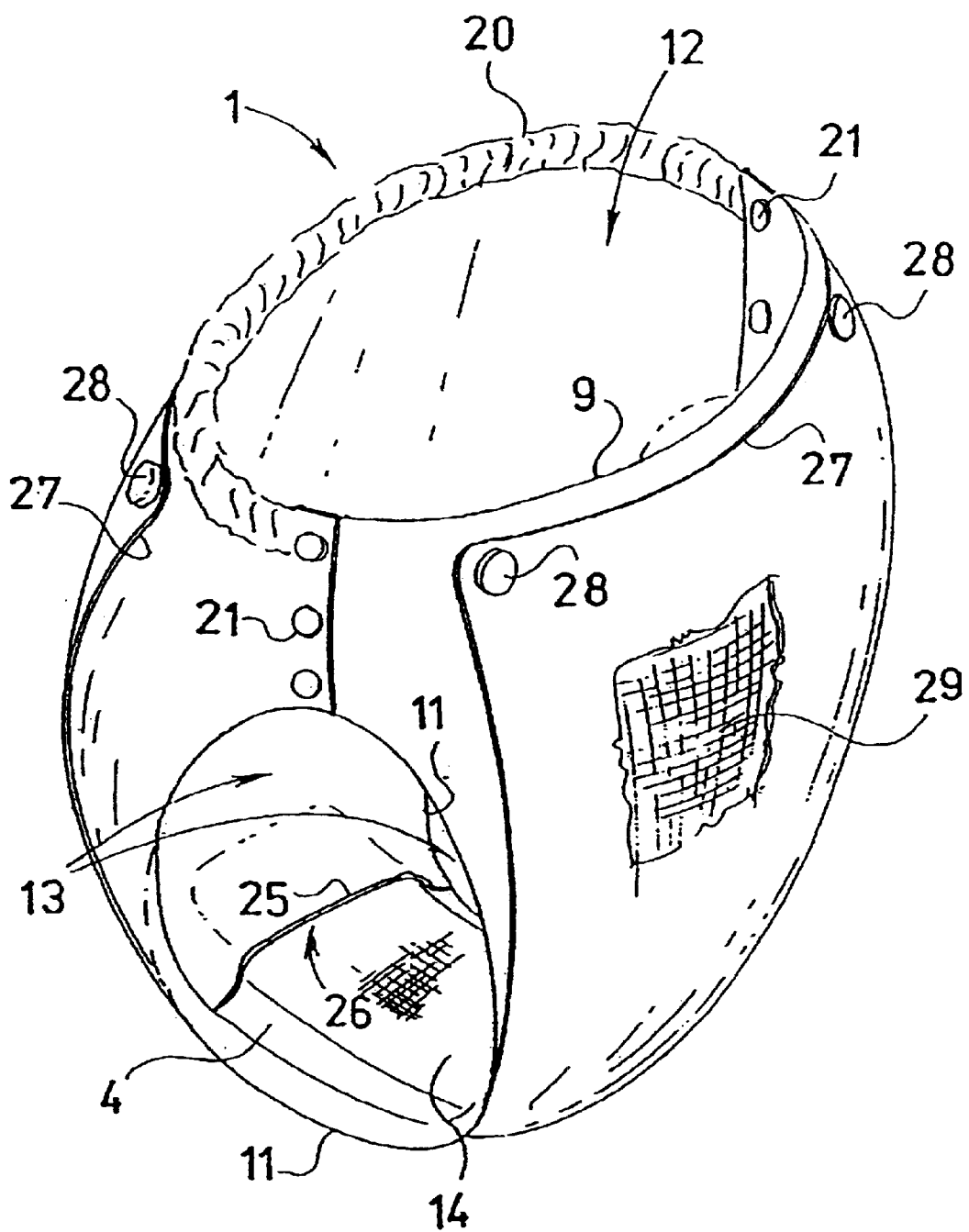
FIG. 2—shows a diaper pants in a ready-to-use condition, along with a therapeutic diaper.
Figure 3:
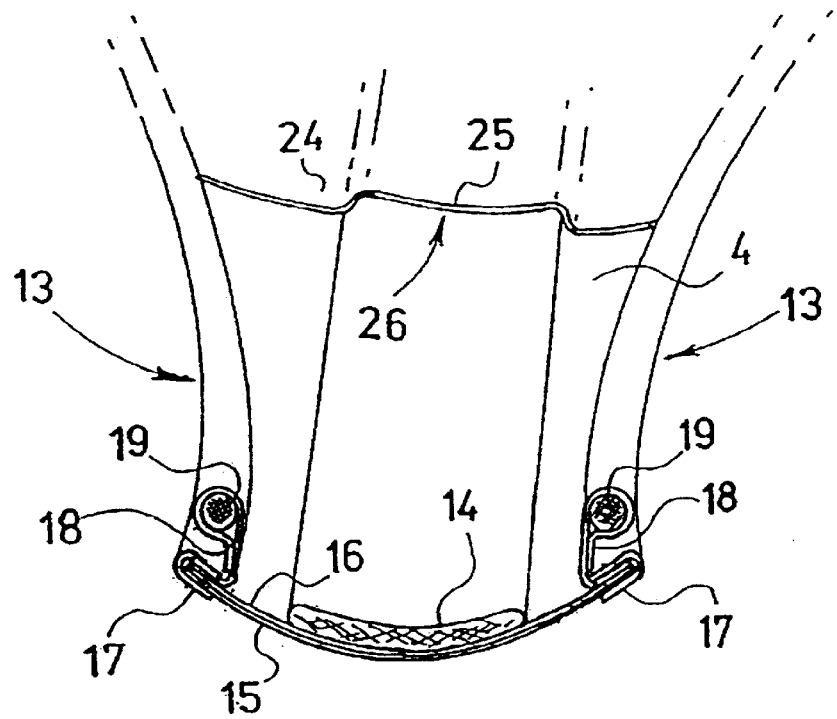
FIG. 3—shows a diaper pants crotch part sectional view.
Figure 4:
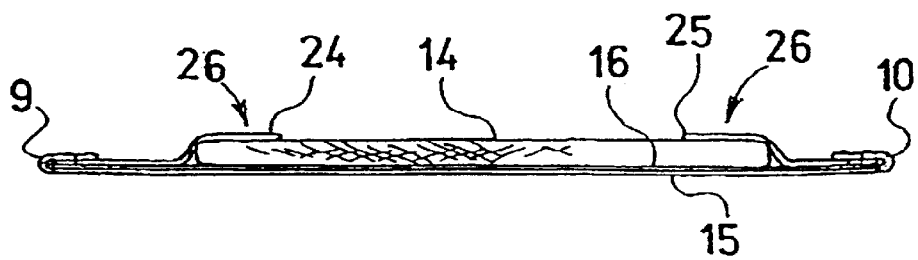
FIG. 4—shows a diaper pants longitudinal sectional view.

The diaper pants 1 have a front part 2, intended to be placed forwards on the user's body, a back part 3, intended to be placed backwards on the the user's body, and a crotch part 4 which connects the front part 2 and the back part 3 and will be located between the user's thighs. The back part 3 has two side peripheral parts 5, 6, running in a direction out of the width W of the back part 3. On the side peripheral parts 5, 6, there are side edges 7 and 8, the front part 2 has two side edges 22 and 23. The parts 2 and 3 further have transverse end edges 9 and 10. The crotch part 4 has two side edges 11. As can be seen from FIG. 2, showing the diaper panties 1 in an assembled condition, the diaper pants 1 have a waist hole 12 between respective transverse end edges 9 and 10, and two leg holes 13 surrounded by side edges 11 of the crotch part 4.

The diaper pants 1 consist of two material layers, cut to a respective shape, seen on FIG. 1, with allowances for making side edges 7, 8, 22, 23 and end edges 9, 10 with the first, lower material layer. The first layer 15 of the material forms the outer face side of the pants 1, while the other material layer 16 forms the inner face side of the pants 1. The first layer 15 and the second layer 16 are placed on each other and hemmed with a hemming strip 17.

In a crotch part 4 into each hemming strip 17 in the region of leg holes 13 a portion 18 with an elastic hem 19 is sown to for better placement of the diaper pants 1 on the user's body and against the side leakage of not absorbed body liquids.

The transverse end edge 10 of the back part 3 is formed by folding the material allowance length 15 over the second layer 16 edge towards inside and stitching through all three layers together, whereby a hollow edge is originated, wherein an elastic member 20 is arranged adjacent to the back and hips of the user. The transverse end edge 9 of the front part 2 is formed by a similar folding and securing of the layer 15, however, it is solid and inelastic.

To assemble the diaper pants 1 into a shape for its use, the fastening means 21 are arranged on the front part 2 and the back part 3. One half of the fastening means 21 is arranged on the side edges 7 a 8 of side parts 5 and 6. The side edges 7 a 8 are strengthened and reinforced for that purpose, for safe fastening of means 21, which are in this case metal snapping buttons for mechanical fastening. The strengthening is effected in a similar manner like folding material allowances of the first layer 15 and fastening with the second layer 16, as mentioned with the end edges 9 and 10. The same strengthened side edges 22 and 23 are created even on the front part 2 and within them the second half of the fastening means 21 is secured.

Further, the diaper pants contain a replaceable absorbent pad 14. This pad 14 is of a common construction. The face side of the diaper pants 1 is provided, to receive the pad 14, with bands 24 extending over the whole width of the front part 2 and the back part 3 of the diaper pants 1. The bands 24 are stitched do the transverse end edges 9 and 10 of the front part 2 and the back part 3 and to the side edges 7, 8 and 22, 23. The inner transverse free edges of bands 24 are hemmed by an inelastic strip 25. The bands 24 form pockets 26 for inserting the absorbent pad 14.

To the face side of the diaper pants 1 a takeable apart outer rectangular housing 27 is positioned. This housing 27 is closed on its front transverse end edge, adjacent to the end transverse edge 9 of the front part 2, while the opposite back transverse end edge, adjacent to the end transverse edge 10 of the back part 3, is open. The rectangular housing 27 is on its both transverse end edges secured to the transverse end edges 9 and 10 of the front part 2 and the back part 3 with buttons 28 stitched on the end edges 9 and 10, while the holes for the buttons 28 are formed in the front transverse end edge of the housing 27, in its corners, as well as in both layers of the back transverse end edge, again in its corners. The side peripheral parts 5, 6, of the back part 3 stay free, i.e., the rectangular housing 27 covers only a central part of the diaper pants 1. The length dimension of the rectangular housing 27 corresponds to the diaper pants 1 length, while the transverse dimension corresponds substantially to the front part 2 width. The dimensions of the housing 27 and its thickness are, of course, such that they correspond to the orthopaedic aid 29 dimensions.

Within the rectangular housing 27 a changeable orthopaedic pad 29 is located destined for prevention or actual treatment of various hip joints deformations, e.g., hip joints dysplasia. It is made of a firm elastic material. The pad 29 dimensions are adjusted to the desired therapeutic position of the wearer's thighs given by the thighs orientation to the desired position with an inclination taking consideration to the pelvis and to the side inclinations of thighs.

The diaper pants according to the invention maintain properties of known diaper panties with a replaceable pad. The diaper pants holding system is very simple and provides for sufficient strength and elasticity of the panties and excludes their spontaneous opening. Even the not absorbed body fluids discharge is prevented, as well as soiling the user's clothing. Any commonly known diaper of a quality absorbent material with suitable characteristics can be used as an absorbent diaper. The diaper panties can serve as pants, diaper pants or diaper pants with an orthopaedic pad for prevention and abnormalities treatment. The orthopaedic pad is of such a size and location that it sits safely on a desired place when used. The pants are of a multipurpose nature.

What is claimed is:

1. Children's absorbent diaper pants, with a therapeutic orthopaedic pad, having a front part /2/, a back part /3/ with an elastic member /20/ in the waist hole /12/ region, and a crotch part /4/ with elastic hems /19/ in the diaper pants /1/ leg holes, wherein the front part /2/ and the back part /3/ are provided with fastening means /21/, and on the diaper pants /1/ inner surface side a changeable absorbent pad /14/ is arranged, and the diaper pants /1/ are further provided with a therapeutic orthopaedic pad /29/; characterised in that the orthopaedic pad /29/ is located in a rectangular housing /27/ arranged on the diaper pants /1/ facing side, while this housing /27/ is by its front and back transverse ends, in a takeable apart manner, fastened to the end edges /9, 10/ of the front part /2/ and of the back part /3/, and an absorbent pad /14/ is inserted inside retaining means.

2. Diaper pants according to claim 1, characterised in that the orthopaedic pad /29/ is of a firm elastic material and is arranged, changeably, in the rectangular housing /27/.

3. Diaper pants according to claim 1, characterized in that the rectangular housing /27/ has a longitudinal dimension corresponding to the diaper panties /1/ length and a transverse dimension corresponding to their front part /2/ width, and the housing /27/ is closed at its front transverse end edge, adjacent to the front part /2/ end edge /9/, while the opposite back transverse end edge, adjacent to the back part /3/ end edge /10/, is open, and the rectangular housing /27/ is on both transverse end edges provided with fastening means for its securing to the diaper pants /1/.

4. Diaper pants according to claim 3, characterised in that the fastening means of the rectangular housing /27/ are formed by buttons /28/, secured on the diaper pants /1/ front /2/ and back /3/ parts end edges /9, 10/, while the holes for the buttons /28/ are made in the corners of the front and back end transverse edges of the rectangular housing /27/.

5. Diaper pants according to claim 1, characterized in that the retaining means for inserting an absorbent pad /14/ are formed in a shape of two pockets /26/, formed by two bands /24/ extending over the whole width of the front /2/ and back /3/ parts and they are anchored in side edges /7, 8, 22, 23/ and in transverse end edges /9, 10/ of the front /2/ and back /3/ parts, while the inner transverse edge of the bands /24/ is free.

6. Diaper pants according to claim 2, characterized in that the rectangular housing /27/ has a longitudinal dimension corresponding to the diaper panties /1/ length and a transverse dimension corresponding to their front part /2/ width, and the housing /27/ is closed at its front transverse end edge, adjacent to the front part /2/ end edge /9/, while the opposite back transverse end edge, adjacent to the back part /3/ end edge /10/, is open, and the rectangular housing /27/ is on both transverse end edges provided with fastening means for its securing to the diaper pants /1/.

7. Diaper pants according to claim 6, characterized in that the fastening means of the rectangular housing /27/ are formed by buttons /28/, secured on the diaper pants /1/ front /2/ and back /3/ parts end edges /9, 10/, while the holes for the buttons /28/ are made in the corners of the front and back end transverse edges of the rectangular housing /27/.

8. Diaper pants according to claim 2, characterized in that the retaining means for inserting an absorbent pad /14/ are formed in a shape of two pockets /26/, formed by two bands /24/ extending over the whole width of the front /2/ and back /3/ parts and they are anchored in side edges /7, 8, 22, 23/ and in transverse end edges /9, 10/ of the front /2/ and back /3/ parts, while the inner transverse edge of the bands /24/ is free.

9. Diaper pants according to claim 3, characterized in that the retaining means for inserting an absorbent pad /14/ are formed in a shape of two pockets /26/, formed by two bands /24/ extending over the whole width of the front /2/ and back /3/ parts and they are anchored in side edges /7, 8, 22, 23/ and in transverse end edges /9, 10/ of the front /2/ and back /3/ parts, while the inner transverse edge of the bands /24/ is free.

10. Diaper pants according to claim 6, characterized in that the retaining means for inserting an absorbent pad /14/ are formed in a shape of two pockets /26/, formed by two bands /24/ extending over the whole width of the front /2/ and back /3/ parts and they are anchored in side edges /7, 8, 22, 23/ and in transverse end edges /9, 10/ of the front /2/ and back /3/ parts, while the inner transverse edge of the bands /24/ is free.

11. Diaper pants according to claim 4, characterized in that the retaining means for inserting an absorbent pad /14/ are formed in a shape of two pockets /26/, formed by two bands /24/ extending over the whole width of the front /2/ and back /3/ parts and they are anchored in side edges /7, 8, 22, 23/ and in transverse end edges /9, 10/ of the front /2/ and back /3/ parts, while the inner transverse edge of the bands /24/ is free.

12. Diaper pants according to claim 7, characterized in that the retaining means for inserting an absorbent pad /14/ are formed in a shape of two pockets /26/, formed by two bands /24/ extending over the whole width of the front /2/ and back /3/ parts and they are anchored in side edges /7, 8, 22, 23/ and in transverse end edges /9, 10/ of the front /2/ and back /3/ parts, while the inner transverse edge of the bands /24/ is free.

* * * * *